United States Patent
Kojima et al.

[11] Patent Number: 5,869,276
[45] Date of Patent: Feb. 9, 1999

[54] METHOD FOR DETERMINATION OF DIRECT BILIRUBIN AND REAGENT THEREFOR

[75] Inventors: Ryo Kojima; Yoshikiyo Sasagawa; Yasunori Okazaki, all of Koriyama; Takeshi Nagasawa, Urawa, all of Japan

[73] Assignee: Nitto Boseki Co., Ltd., Fukushima, Japan

[21] Appl. No.: 90,332

[22] Filed: Jun. 4, 1998

[30] Foreign Application Priority Data

Jun. 6, 1997 [JP] Japan ................................ 9-163524
Jul. 4, 1997 [JP] Japan ................................ 9-193303

[51] Int. Cl.[6] .............................. C12Q 1/26; C12Q 1/00; G01N 33/53
[52] U.S. Cl. .............................. 435/25; 435/4; 435/961; 435/28
[58] Field of Search ................................ 435/25, 4, 961, 435/28

Primary Examiner—Louise N. Leary
Attorney, Agent, or Firm—Armstrong, Westerman, Hattori, McLeland & Naughton

[57] ABSTRACT

There is provided a method for determination of direct bilirubin which comprises the steps of contacting a bilirubin oxidase with a sample suspected of containing bilirubin; and, measuring direct bilirubin in the sample by optical changes of the sample, characterized in that bilirubin oxidase is allowed to act in the presence of a indirect bilirubin reaction inhibitor selected from a thiocyanate ion, a hydrazide, reduced nicotinamide adenine dinucleotide, reduced nicotinamide adenine dinucleotide phosphate and a potassium ion of 100 mM to 800 mM. By completely avoiding interference of indirect bilirubin, direct bilirubin is selectively and precisely determined using a reagent kit in the form of solution. The method and reagent of the invention are safe and free of environmental pollution due to unnecessary waste liquid treatment.

3 Claims, 9 Drawing Sheets

METHOD FOR DETERMINATION OF DIRECT BILIRUBIN AND REAGENT THEREFOR

BACKGROUND OF THE INVENTION

1. Field of the Invention

The present invention relates to a method for determination of direct bilirubin contained in a sample of body fluid and a reagent for use in the method.

2. Related Art

Bilirubin is a metabolic product of hemoglobin derived from aged erythrocyte and is the main component of bile pigment. Blood bilirubin contains as predominant components direct bilirubin (conjugate form) and indirect bilirubin (free form). Direct bilirubin having propionic acid groups on the side chain, which enzymatically forms an ester bond mainly with glucuronic acid in the liver, is highly water soluble, and reacts readily with a diazo reagent to form an azo dye substance. Indirect bilirubin, the propionic acid groups of which are in a free state, has a low water solubility and reacts with a diazo reagent only in the presence of a reaction accelerator such as an alcohol, etc. Indirect bilirubin can be determined by subtracting direct bilirubin from total bilirubin which is a measurement value of conjugated form and free form in total, obtained by a diazo reaction with a diazo reagent in the presence of a reaction accelerator.

Individual bilirubin concentrations of conjugate (direct) form and free (indirect) form can thus be separately determined to make diagnosis of various liver diseases and diacrisis of jaundice. Therefore, the measurement of bilirubin is one of important clinical tests.

There have been proposed methods for quantitative determination of direct bilirubin as described below, such as a method using a diazo reagent, a method using bilirubin oxidase, a method using high performance liquid chromatography, a method using a chemical oxidizing substance, and the like.

A) Assay for direct bilirubin using a diazo reagent

In the diazo method, bilirubin reacts with a diazo reagent to form azobilirubin. The azobilirubin has an absorption maximum which is higher than the visible absorption maximum of bilirubin itself and is easily detectable by optical changes. The method using a diazo reagent has many variations due to a kind of a reaction accelerator for indirect bilirubin, conditions for reaction termination and conditions for detecting azobilirubin (Malloy, H. T., Evelyn, K. A.: J. Biol. Chem., 119, 481 (1937); The determination of bilirubin with the photoelectric calorimeter; Jendrassik, L., Grof, P., Biochem. Z., 297, 81 (1938): Vereinfachte Photometrische Methoden zur Bestimmung des Blutbilirubins; Micha elsson, M., Scand. J. Clin. Lab. Invest., 12 (Supp. 56), 1–80 (1937): Bilirubin determination in serum and urine).

B) Assay for direct bilirubin using bilirubin oxidase

In the method using a bilirubin oxidase, the enzyme is acted on a sample suspected of containing bilirubin to oxidize bilirubin to biliverdin, whereupon absorbance of bilirubin disappears in the maximum absorption wavelength region. Direct bilirubin can thus be determined by this decrease in the absorbance. Various modifications have been made to inhibit a reaction of indirect bilirubin. The following methods are proposed for such modifications.

B1) Method for determination of direct bilirubin in which a bilirubin oxidase is reacted in a pH range of 3.5 to 4.5 (Japanese Patent KOKAI (Laid-Open) No. 59-125899);

B2) Method for determination of direct bilirubin which involves reacting a bilirubin oxidase with bilirubin in an acidic buffer solution of pH 5 to 6 containing an anionic surfactant (Shogo Otsuji: Clin. Biochem., 21, 33–38 (1988) and Japanese Patent KOKAI (Laid-Open) No. 60-152955);

B3) Method for quantitative determination of conjugated bilirubin which involves reacting a bilirubin oxidase in a buffer solution of pH 9 to 10 and measuring a change in absorbance (Japanese Patent KOKAI (Laid-Open) No. 62-58999);

B4) Method for quantitative determination of direct bilirubin which involves reacting a bilirubin oxidase in a buffer solution of pH 2.0 to 3.3 containing potassium ferrocyanide and/or potassium ferricyanide and measuring a change in absorbance (Japanese Patent KOKAI (Laid-Open) No. 64-5499);

B5) Method for quantitative determination of direct bilirubin which involves reacting a bilirubin oxidase in the presence of a fluorine compound or a reducing agent (Japanese Patent KOKAI (Laid-Open) No. 5-276992); and B6) Method for quantitative determination of direct bilirubin which involves allowing to act a bilirubin oxidase in the presence of a tetrapyrrole compound (Japanese Patent KOKAI (Laid-Open) No. 7-231795).

C) Method for determination of direct bilirubin using high performance liquid chromatography (HPLC)

The method using HPLC involves elution of bilirubin by an organic solvent gradient on a reversed phase column and fractionation of the bilirubin fractions due to difference in the hydrophilic/hydrophobic property. According to HPLC, serum bilirubin is fractionated into 4 fractions of $\alpha$, $\beta$, $\gamma$ and $\delta$. The $\alpha$, $\beta$, $\gamma$ and $\delta$ fractions are identified, respectively, to free form of bilirubin, bilirubin in which only one of the two propionic acid groups on the side chain in one molecule forms an ester bond with glucuronic acid (bilirubin monoglucuronide), bilirubin in which the two propionic acid groups form ester bonds with glucuronic acid (bilirubin diglucuronide) and bilirubin which forms covalent bond to albumin. The $\delta$ fraction is assumed to be formed by non-enzymatic reaction of the $\gamma$ fraction with albumin (Toshio Yamamoto, Nippon Naibunpi Gakkai Zasshi, 78 (11), 36–41 (1989)). It is recognized that the $\alpha$ fraction obtained by HPLC corresponds to indirect bilirubin and the $\beta$ and $\gamma$ fractions correspond to direct bilirubin, when determined by the method using a diazo reagent (John J. Lauff, Clin. Chem., 28 (4) 629–637 (1982)). The method using HPLC has been continuously modified to improve complicated pretreatment of a sample and such modifications are reported in Nakamura, H.: Bunseki Kagaku, 36, 352–355 (1987); Yukihiko Adachi: Gastroenterologia Japonica, 23 (3), 268–272 (1988); Yuko Kato: Kinkidaigaku Igaku Zasshi, 14 (1), 97–112 (1989).

D) Assay for direct bilirubin using a chemical oxidizing agent

The method using a chemical oxidizing agent involves reacting a low molecular oxidizing agent in lieu of a bilirubin oxidase to oxidize bilirubin to biliverdin. When oxidized, the absorbance of bilirubin decreases. Accordingly, direct bilirubin can be determined based on the decreased absorbance. Various modifications have been also made in this method for inhibiting a reaction of indirect bilirubin. The following methods are proposed for such modifications.

D1) Method for quantitative determination of direct bilirubin characterized in that copper ions and thiourea or a derivative thereof are reacted with a sample solution (Japanese Patent KOKAI (Laid-Open) No. 63-118662).

D2) Method for quantitative determination of bilirubin characterized in that vanadic acid ions or trivalent manganese ions are reacted as an oxidizing agent to measure optical changes of a sample solution (Japanese Patent KOKAI (Laid-Open) No. 5-18978). In order to measure direct bilirubin by this method, one or more compounds selected from the group consisting of hydrazines, hydroxylamines, oximes, aliphatic polyvalent amines, phenols, water soluble high molecular weight substances and non-ionic surfactants having an HLB of at least 15 is/are employed as a reaction inhibitor for indirect bilirubin.

D3) Method for quantitative determination of bilirubin characterized in that nitrous acid is reacted as an oxidizing agent to measure optical changes of a sample solution (WO 96-17251). To effect the measurement of the direct bilirubin by this method, a reaction inhibitor for indirect bilirubin such as polyoxyethylene (n-alkyl or iso-alkyl) ether having an HLB of 12 to 15, thiourea, hydrazine, polyvinylpyrrolidone, or the like is employed.

Every one of these methods A) to D) has both advantageous and disadvantages and none of them has been completely satisfactory for the bilirubin assay required. The disadvantages involved in these methods are described below.

In the method A) using a diazo reagent, a reaction in the absence of any reaction accelerator is called a diazo direct reaction, from which the term direct bilirubin originates. However, it has been reported in many journals that a part of indirect bilirubin could also cause this diazo direct reaction (e.g., Killenberg, P. G., Gastroenterology, 78, 1011–1015 (1980); Blankaert, N., J. Lab. Clin. Med., 96, 198–212 (1980); Yukio Manabe, BUNSEKI KAGAKU, 30, 736–740 (1981); Chan, K. M., Clin. Chem., 31, 1560–1563 (1985); Akira Kosaka, KENSA-TO-GIJUTSU, 14, 971–975 (1986); Yukihiko Adachi, SEIBUTSU-SHIRYOU BUNSEKI, 9, 33–42 (1986)). Therefore, even though bilirubin is determined by the so-called diazo direct method, the thus obtained bilirubin value does not strictly represent "direct bilirubin".

The method B) using a bilirubin oxidase has been developed to obtain bilirubin values as close to the measurement values defined by the direct diazo reaction as possible. As a natural consequence, oxidation is also caused partly with indirect bilirubin and hence basically, the method B) does not give precise measurement of "direct bilirubin". This has necessitated modifications of the method B) to avoid any undesirable reaction with indirect bilirubin. In an improved method, a bilirubin oxidase is allowed to act in the presence of a fluorine compound (Japanese Patent KOKAI (Laid-Open) No. 5-276992) and in another method a bilirubin oxidase is allowed to act in the presence of a tetrapyrrole compound (Japanese Patent KOKAI (Laid-Open) No. 7-231795). However, these methods encounter problems that use of a fluorine compound results in environmental pollution in the former and the necessity for the tetrapyrrole compound to be present in a reagent solution makes the solution unstable which does not enable to use the assay system in a solution state for time required for the assay.

The method C) using HPLC provides a high efficiency of analysis but on the other hand requires a considerably long time for about an hour to treat one sample. Therefore, the method C) is inadequate for treating a large number of samples. Moreover, the method C) requiring expensive and special apparatuses is not available for all purposes.

The method D) using a chemical oxidizing agent involves similar problems as observed in the method B) using a bilirubin oxidase, since the method D) has also been developed to obtain bilirubin measurement values as close to those defined by the direct diazo reaction as possible and hence, a part of indirect bilirubin is oxidized. In this regard, it is difficult to say that the method D) precisely measures "direct bilirubin".

As stated above, none of the foregoing methods can perfectly avoid the interference of indirect bilirubin or can provide stable and safe measurement of direct bilirubin. Therefore, it has been strongly desired to develop a method for determination of direct bilirubin deprived of these defects in the prior art and satisfying all the requirements.

SUMMARY OF THE INVENTION

The present invention has been accomplished in view of the current situation. According to the present invention, there is provided a safe and stable method for determination of direct bilirubin, in which interference of indirect bilirubin can be fully avoided, and there is no danger to environmental pollution such as a waste water treatment, etc.

The present inventors have extensively studied the reactivity of indirect and direct bilirubins in an optimum pH range of a bilirubin oxidase. As a result it has been discovered that when a bilirubin oxidase is allowed to act on bilirubin in the presence of a thiocyanate ion, a hydrazide, reduced nicotinamide adenine dinucleotide (hereinafter often abbreviated as NADH), reduced nicotinamide adenine dinucleotide phosphate (hereinafter often abbreviated as NADPH) or a potassium ion of 100 mM to 800 mM, interference of indirect bilirubin due to its oxidation can be completely inhibited and at the same time, oxidation of direct bilirubin can selectively proceed quantitatively. Then, direct bilirubin can be precisely determined. The present invention has thus been established.

The present invention relates to a method for determination of direct bilirubin which comprises contacting a bilirubin oxidase with a sample of body fluid and measuring direct bilirubin in the sample by optical changes of the sample, characterized in that the bilirubin oxidase is allowed to act in the presence of at least one reaction inhibitor for indirect bilirubin selected from a thiocyanate ion, a hydrazide, NADH, NADPH and a potassium ion of 100 mM to 800 mM.

The present invention also relates to a reagent kit for measurement of direct bilirubin comprising as essential ingredients:

i) a bilirubin oxidase; and, ii) at least one reaction inhibitor for indirect bilirubin selected from a thiocyanate ion, a hydrazide, NADH, NADPH and a potassium ion of 100 mM to 800 mM.

DETAILED DESCRIPTION OF PREFERRED EMBODIMENTS

In the present invention, samples to be assayed are not particularly limited so long as these samples are suspected of containing direct bilirubin or indirect bilirubin. In general, the samples include those from living body fluids such as plasma, serum, urine, etc. and model samples thereof.

In the present invention, the thiocyanate ion which is used as the reaction inhibitor for indirect bilirubin includes, but not particularly limited to, an alkali metal thiocyanate, an alkaline earth metal thiocyanate, ammonium thiocyanate, etc., with sodium thiocyanate and potassium thiocyanate being preferred.

The hydrazide for use in the present invention includes, but not particularly limited to, acetyl hydrazide, phthalic hydrazide, isophthaloyl dihydrazide, terephthalic dihydrazide, benzenesulfonyl hydrazide, etc.

Reduced nicotinamide adenine dinucleotide (NADH) or reduced nicotinamide adenine dinucleotide phosphate (NADPH) may be incorporated into the reaction reagents. Alternatively, NADH or NADPH may also be derived from oxidized nicotinamide adenine dinucleotide through an enzymatic reaction using an alcohol dehydrogenase, a glucose-6-phosphate dehydrogenase, etc., as far as the function required in the present invention can be achieved.

The potassium ion for use in the present invention includes, but not particularly limited to, potassium chloride, potassium bromide, potassium acetate, potassium citrate, potassium tartarate, potassium lactate, potassium phthalate, potassium sulfate, etc.

In the present invention, the reaction inhibitor for indirect bilirubin should be present in an optimum concentration in the reaction solution where oxidation proceeds. At too low a concentration, the effect of inhibiting the reaction of indirect bilirubin may be insufficient, whereas at too high a concentration, the action of a bilirubin oxidase may become excessive to rather interfere the oxidation of direct bilirubin. Therefore, when the thiocyanate ion or the hydrazide is used as the reaction inhibitor for indirect bilirubin, the concentration is maintained preferably in a range of 0.1 mM to 100 mM, more preferably 0.2 mM to 50 mM, in the enzyme reaction solution.

Where NADH or NADPH is used as the reaction inhibitor, the concentration is generally in a range from 0.1 mM to 10 mM, preferably 0.2 mM to 5 mM.

In the case of using the potassium ion as the inhibitor, the concentration is preferably in a range of 100 mM to 800 mM, more preferably 110 mM to 600 mM, most preferably 120 mM to 400 mM, in the ultimate reaction solution. Where the potassium ion concentration is less than 100 mM, the effect of inhibiting the reaction of indirect bilirubin is insufficient. On the other hand, with the concentration more than 800 mM, the inhibiting activity of a bilirubin oxidase increases so that the oxidation of direct bilirubin tends to be interfered.

In the method of the present invention, the indirect bilirubin reaction inhibitors are effective when used alone, but the effect is often improved by use in combination of two or more. For example, at least two inhibitors selected from the thiocyanate ion, hydrazide, NADH and NADPH may be used in combination. Alternatively, one or more inhibitors selected from the thiocyanate ion, hydrazide, NADH and NADPH may be used in combination with the potassium ion.

In the method of the present invention, the bilirubin oxidase for use in the present invention includes, but not particularly limited to, bilirubin oxidase originating from *Myrothecium verrucaria* (commercially available from Amano Pharmaceutical Co., Ltd.), bilirubin oxidase from *Trachyderma tsunodae* (commercially available from Takara Shuzo Co., Ltd.), bilirubin oxidase derived from the genus Pleurotus (commercially available from K. K. Seishin), and the like. It is desirable to use the enzyme in a concentration of 0.001 to 10 U/ml, preferably 0.01 to 1 U/ml, more preferably 0.02 to 0.5 U/ml, in the ultimate reaction solution.

When a bilirubin oxidase is contacted with a sample of body fluid, its pH range is not particularly limited insofar as the enzymatic activity can be displayed under the optimum conditions for a bilirubin oxidase. However, the pH range is preferably from 4.5 to 6.5, more preferably 5.0 to 6.0. Any buffer solution can be used in the present invention without any particular limitation, if the solution has a buffering effect in the pH range identified above. Specific examples of such a buffer solution are a potassium hydrogen phthalate/sodium hydroxide buffer solution, a sodium citrate/sodium hydroxide buffer solution, a malic acid/sodium hydroxide buffer solution, etc. Above all, a buffer solution containing a potassium salt such as potassium hydrogen phthalate or the like is preferred since the potassium ion has the effect of inhibiting the reaction of indirect bilirubin.

According to the present invention, direct bilirubin contained in a sample can be selectively assayed using the reagent kit for measurement of direct bilirubin comprising, e.g., a bilirubin oxidase and at least one of indirect bilirubin reaction inhibitors.

A preferred reagent kit for measurement of direct bilirubin comprises two reagents of a first reagent solution comprising, e.g., thiocyanate ions or the hydrazide and a second reagent solution comprising a bilirubin oxidase. More preferably, the first reagent solution further contains potassium ions.

In another embodiment of the reagent kit, the kit is designed to divide the necessary reagent components into two solutions because of the stability of NADH, NADPH or a bilirubin oxidase. Thus, a first reagent solution contains, for example, a buffer solution having a pH of 4.5 to 6.5, preferably a pH of 5.0 to 6.0 and a second reagent solution contains a bilirubin oxidase and NADH, NADPH or potassium ions. Where NADH or NADPH is used, the second reagent solution has preferably a pH of 9 or more, more preferably 9 to 11.0, in view of the stability of NADH or NADPH in its solution state. More preferably, the second reagent solution further contains potassium ions.

Where potassium ions are singly employed as a reaction inhibitor for indirect bilirubin, the pH range of the second reagent solution containing bilirubin oxidase is maintained preferably from 7 to 11, in view of the stability of bilirubin oxidase.

Representative examples of the buffer solution are a potassium hydrogen phthalate/sodium hydroxide buffer solution, a sodium citrate/sodium hydroxide buffer solution, a malic acid/sodium hydroxide buffer solution, etc.

In a more preferred embodiment, the first reagent solution further contains potassium ions.

In accordance with the present invention, direct bilirubin can be determined as follows, using the kit described above. A sample is mixed with a first reagent solution. An absorbance at a specific wavelength, preferably at 450 nm in a wavelength region (430–460 nm) based on the bilirubin in the solution to obtain the measurement value as "Absorbance 1". Next, a second reagent solution containing a bilirubin oxidase is added to the solution to conduct oxidation at 25° to 40° C. for 3 to 15 minutes. Then, an absorbance at a specific wavelength based on the bilirubin in the solution is again measured to obtain the measurement value as "Absorbance 2". After the Absorbance 1 and Absorbance 2 are corrected for the solution volume, a change in absorbance before and after the oxidation is determined. The direct bilirubin concentration in the sample can be determined from the change in absorbance and a calibration curve prepared in advance on the basis of changes in the absorbance obtained by the same procedures above, using standard solutions of known concentrations of bilirubin. The method of the present invention for determination of direct bilirubin is applicable to versatile automatic analyzers commercially available for clinical tests, such as Hitachi Model 7070 Automatic Analyzer, etc. The sample solution is preferably used in a volume of 0.005 to 1 ml.

The thiocyanate ions, hydrazides and potassium ions, which are used in the reagents for determination of direct bilirubin, are not very unstable in an aqueous solution. However, when a pH is maintained at 9 or more, NADH or NADPH and a bilirubin oxidase are stable in an aqueous solution. Therefore, the reagent of the present invention can be provided as a liquid reagent in the form of an aqueous solution.

The reagent for determination of direct bilirubin may further contain other known reagents such as an antiseptic, a chelating agent, a surfactant, etc., so long as they can be used in conventional reagents or reagents kit. These known reagents may be used in the reagent of the invention, upon proper selection according to the known procedures.

EXAMPLES 1 THROUGH 6 AND COMPARATIVE EXAMPLE 1

Effect of inhibiting the reaction of indirect bilirubin

Figure 1:
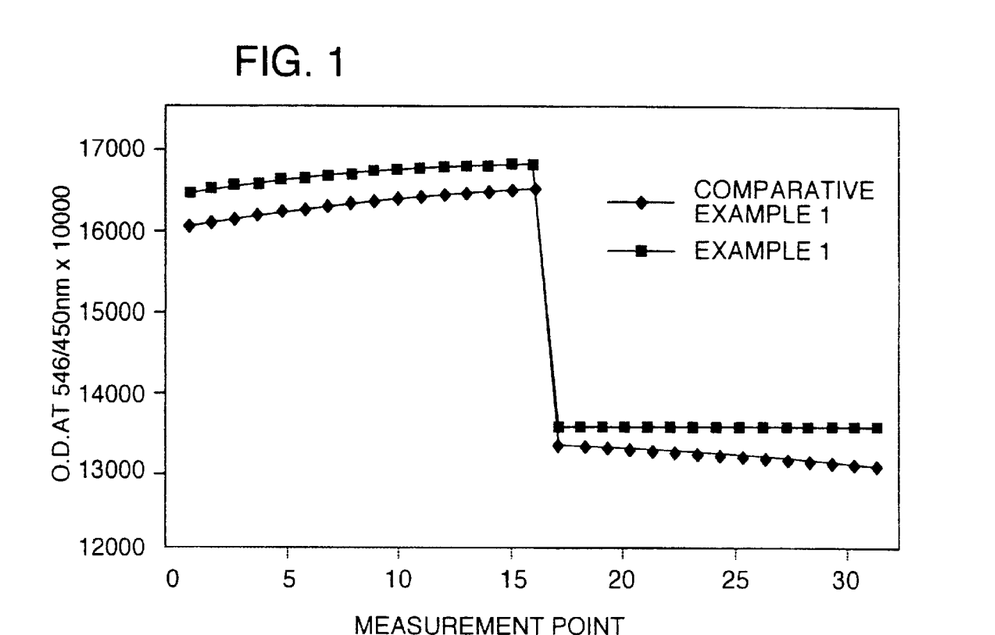
FIG. 1 shows reaction time courses in Example 1 and Comparative Example 1, wherein measurement points (ca. 20 seconds/point) are given on the abscissa and absorbance× 10000 is given on the ordinate.
Figure 2:
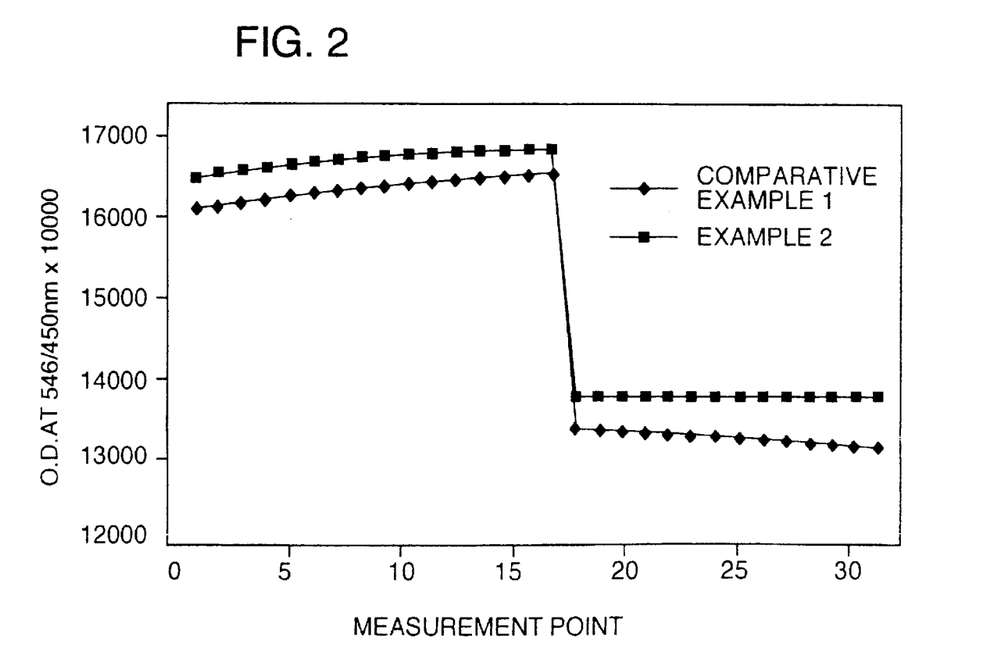
FIG. 2 shows reaction time courses in Example 2 and Comparative Example 1, wherein measurement points (ca. 20 seconds/point) are given on the abscissa and absorbance× 10000 is given on the ordinate.
Figure 3:
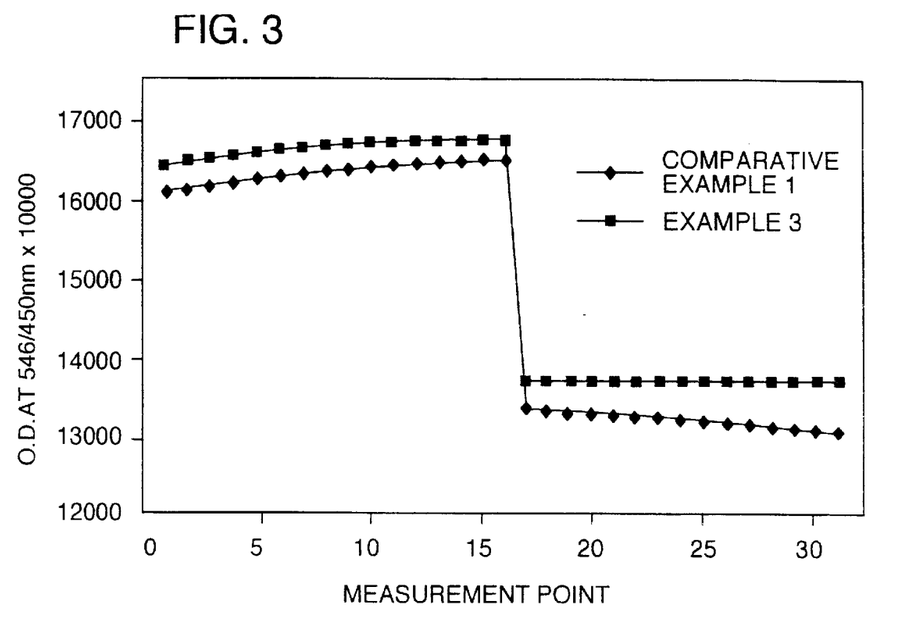
FIG. 3 shows reaction time courses in Example 3 and Comparative Example 1, wherein measurement points (ca. 20 seconds/point) are given on the abscissa and absorbance× 10000 is given on the ordinate.
Figure 4:
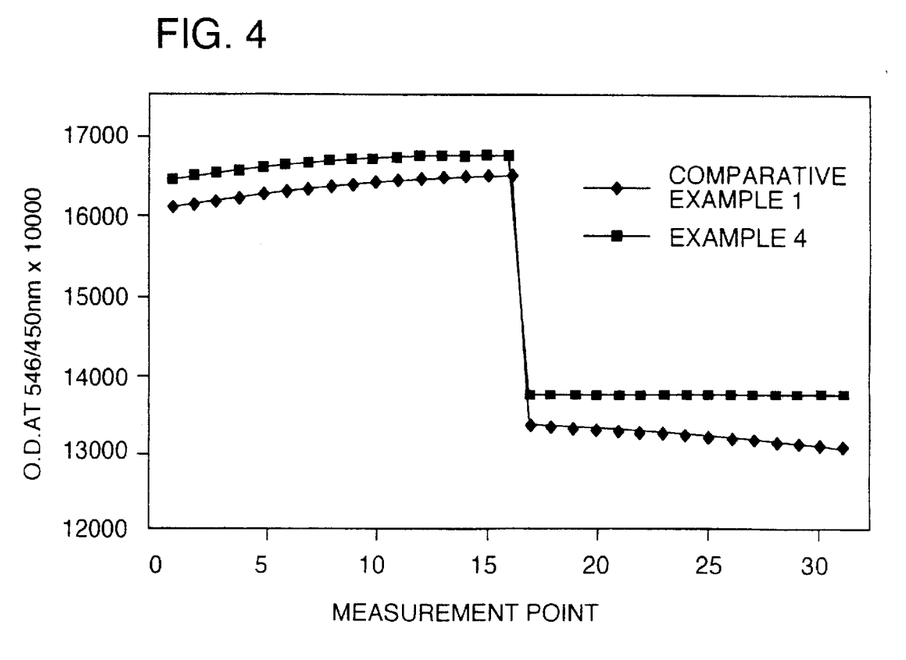
FIG. 4 shows reaction time courses in Example 4 and Comparative Example 1, wherein measurement points (ca. 20 seconds/point) are given on the abscissa and absorbance× 10000 is given on the ordinate.
Figure 5:
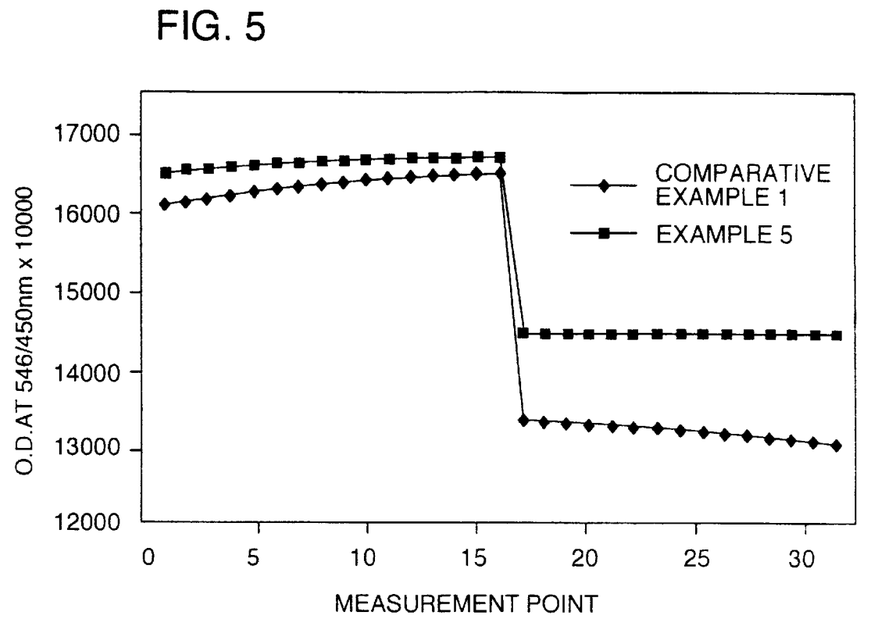
FIG. 5 shows reaction time courses of indirect bilirubin using a bilirubin oxidase in Example 5 and Comparative Example 1, wherein measurement points (ca. 20 seconds/point) are given on the abscissa and absorbance×10000 is given on the ordinate.
Figure 6:
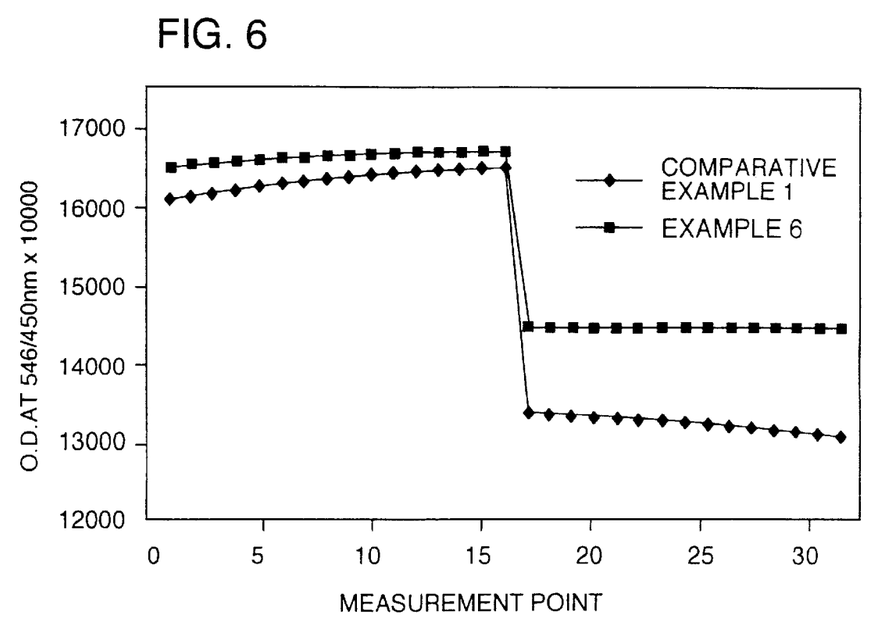
FIG. 6 shows reaction time courses of indirect bilirubin using a bilirubin oxidase in Example 6 and Comparative Example 1, wherein measurement points (ca. 20 seconds/point) are given on the abscissa and absorbance (×10000) is given on the ordinate.

The following experiments are carried out to see if the oxidation of indirect bilirubin is inhibited in the presence of 100 mM to 800 mM of potassium ions (Example 1), thiocyanate ions (Example 2), hydrazides (Examples 3 and 4), NADH (Example 5) or NADPH (Example 6), when oxidized with a bilirubin oxidase. In Comparative Example 1, the same procedures are repeated in the absence of these inhibitors. Details of these reagents, samples and procedures are given below and the results obtained are also shown in the tables below and in the figures.

(1) First and second reagent solutions

| First reagent solution used in Comparative Example 1 | |
| --- | --- |
| Phthalic acid | 150 mM |
| Triton X-100 | 0.05% |
| pH 5.50 (adjusted with NaOH) | |
| First reagent solution used in Example 1 | |
| Phthalic acid | 150 mM |
| Potassium chloride | 200 mM |
| Triton X-100 | 0.05% |
| pH 5.50 (adjusted with NaOH) | |
| First reagent solution used in Example 2 | |
| Potassium hydrogen phthalate | 150 mM |
| Sodium thiocyanate | 10 mM |
| Triton X-100 | 0.05% |
| pH 5.50 (adjusted with NaOH) | |
| First reagent solution used in Example 3 | |
| Potassium hydrogen phthalate | 150 mM |
| Benzenesulfonyl hydrazide | 10 mM |
| Triton X-100 | 0.05% |
| pH 5.50 (adjusted with NaOH) | |
| First reagent solution used in Example 4 | |
| Potassium hydrogen phthalate | 150 mM |
| Isophthaloyl dihydrazide | 10 mM |
| Triton X-100 | 0.05% |
| pH 5.50 (adjusted with NaOH) | |
| First reagent solution used in Examples 5 and 6 | |
| Potassium hydrogen phthalate | 150 mM |
| Triton X-100 | 0.05% |
| pH 5.50 | |
| Second reagent solution used in Comparative Example 1 and Examples 1 through 4 | |
| Tris (hydroxymethyl) aminomethane | 10 mM |
| Bilirubin oxidase | 0.24 U/ml |
| (derived from the genus Pleurotus) | |
| pH 10.2 | |
| Second reagent solution used in Example 5 | |
| Tris (hydroxymethyl) aminomethane | 10 mM |
| NADH | 5 mM |
| Bilirubin oxidase | 0.24 U/ml |
| pH 10.2 | |
| Second reagent solution used in Example 6 | |
| Tris (hydroxymethyl) aminomethane | 10 mM |
| NADPH | 5 mM |
| Bilirubin oxidase | 0.24 U/ml |
| pH 10.2 | |

(2) Sample solution

A solution containing 50 mg/dl of indirect bilirubin and 6.0 g/l of human serum albumin is used as a sample solution. The sample solution is prepared as follows.

After 5 mg of indirect bilirubin is weighed, it is dispersed in 0.4 ml of dimethylsulfoxide and 0.4 ml of 100 mM sodium carbonate solution is added to the dispersion to dissolve indirect bilirubin. Immediately thereafter, the solution is diluted with 9.2 ml of 100 mM Tris buffer (pH 7.00) containing human serum albumin to give the sample solution.

(3) Measurement in Comparative Example 1 and Examples 1 through 6

Using an automatic analyzer Hitachi Model 7070, measurement is carried out. After mixing 10 μl of the sample solution, 300 μl of the first reagent solution and 75 μl of the second reagent solution, all operations are performed automatically and the change in absorbance at the main wavelength of 450 nm and the subsidiary wavelength of 546 nm is measured by the 2 point end method.

In more detail, the sample solution is mixed with the first reagent solution on the automatic analyzer. After incubation at 37° C. for 5 minutes, absorbance based on the bilirubin contained in the mixture is measured at the main wavelength of 450 nm and the subsidiary wavelength of 546 nm (Absorbance 1). Then, the second reagent solution containing bilirubin oxidase is added to the solution mixture, followed by oxidation of bilirubin at 37° C. for 5 minutes. Again absorbance based on bilirubin in the solution is measured at the wavelengths given above (Absorbance 2). The measurement values of Absorbance 1 and Absorbance 2 are corrected for the solution volume. Then, a decrease in the absorbance before and after the oxidation is obtained. These measurements and calculation are all automatically made with the automatic analyzer.

(4) Results obtained in Comparative Example 1 and Examples 1 through 6

The results of a decrease in the absorbance of indirect bilirubin in Comparative Example 1 and Examples 1 through 6 are shown in Table 1. In addition, the reaction time course on the automatic analyzer in Comparative Example 1 and Examples 1 through 6 are also shown in FIGS. 1 through 6, respectively.

TABLE 1

Decrease in absorbance due to indirect bilirubin

| Examples | Decrease in Absorbance (X 10000) |
| --- | --- |
| Comparative Example 1 | 316 |
| Example 1 | −16 |
| Example 2 | −72 |
| Example 3 | −123 |
| Example 4 | −78 |
| Example 5 | −62 |
| Example 6 | −40 |

As clearly noted from the results of Table 1 and FIGS. 1 through 6, in Examples 1 through 6 which performs the method of the present invention, a decrease in the absorbance due to the oxidation of indirect bilirubin is slight and almost within measurement errors permitted for the automatic analyzer. No decrease in the absorbance is appreciated also in the reaction time course. On the other hand, a significant decrease in the absorbance accompanied by the oxidation of indirect bilirubin is noted in Comparative Example 1.

These results reveal that in all the experiments of the present invention, the reaction of indirect bilirubin with the bilirubin oxidase is inhibited in the presence of thiocyanate ions, hydrazides, 100 mM to 800 mM of potassium ions, NADH or NADPH.

EXAMPLES 7 THROUGH 12

Determination of direct bilirubin in a sample containing direct and indirect bilirubins (1) Preparation of sample solution A solution containing 5 mg/dl of ditaurobilirubin (when calculated as bilirubin), which is synthetic conjugated bilirubin, and 6.0 g/l of human serum albumin in 100 mM Tris buffer solution (pH 7.00) is prepared. The solution is used as a direct bilirubin solution. Separately, a solution containing 5 mg/dl of nonconjugated bilirubin and 6.0 g/l of human serum albumin in 100 mM Tris buffer solution (pH 7.00) is prepared. The solution is used as an indirect bilirubin solution. The direct bilirubin solution is diluted with the indirect bilirubin solution to prepare various sample solutions having the same concentration of total bilirubin (5 mg/dl) but having different concentrations in direct bilirubin. Six (6) sample solutions are prepared, in which ratios of direct bilirubin to total bilirubin are 0.0, 0.2, 0.4, 0.6, 0.8 and 1.0, respectively.

(2) Conditions for measurement

A decrease in the absorbance is measured using the same reagents under the same conditions for measurement as described in Examples 1 through 6, except for using the sample solutions prepared in (1) above. The experiments are designated Example 7 (in which potassium ions are used), Example 8 (in which thiocyanate ions are used), Example 9 (hydrazide), Example 10 (hydrazide), Example 11 (NADH) and Example 12 (NADPH), respectively.

(3) Results

Figure 7:
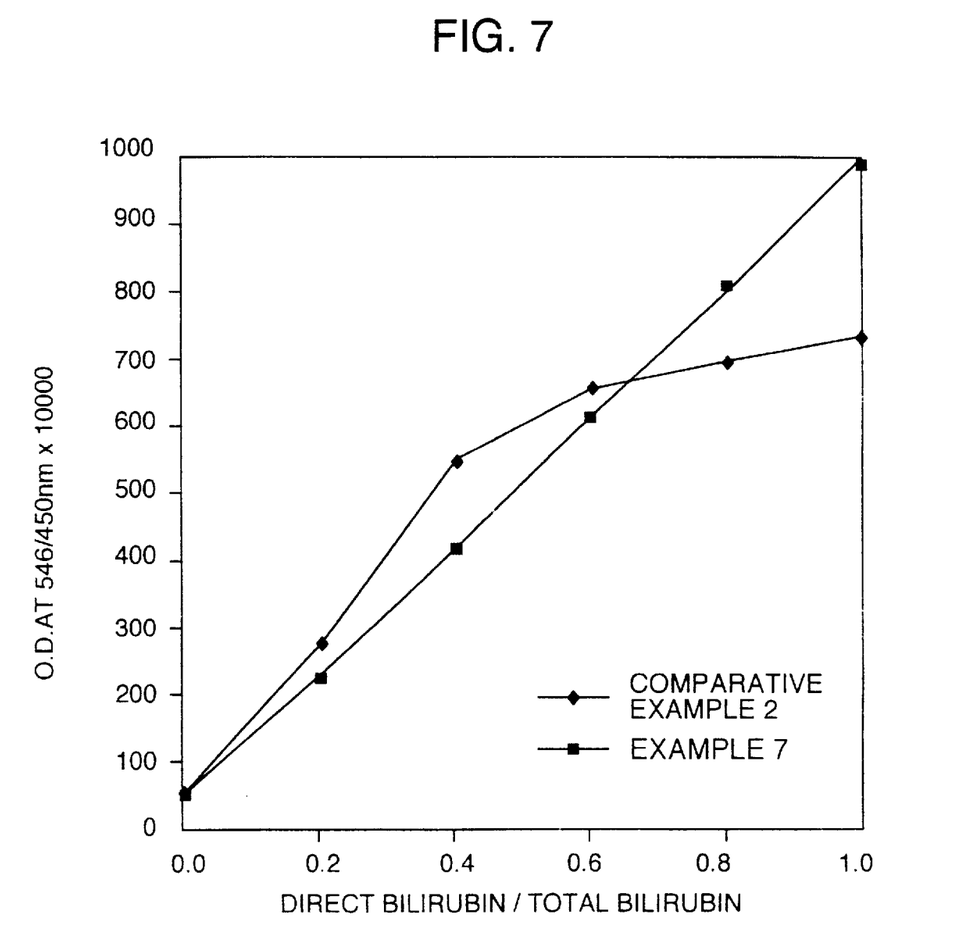
FIG. 7 shows results obtained in Example 7 and Comparative Example 2, wherein a ratio of direct bilirubin to total bilirubin is given on the abscissa and a decrease in the absorbance is given on the ordinate.
Figure 8:
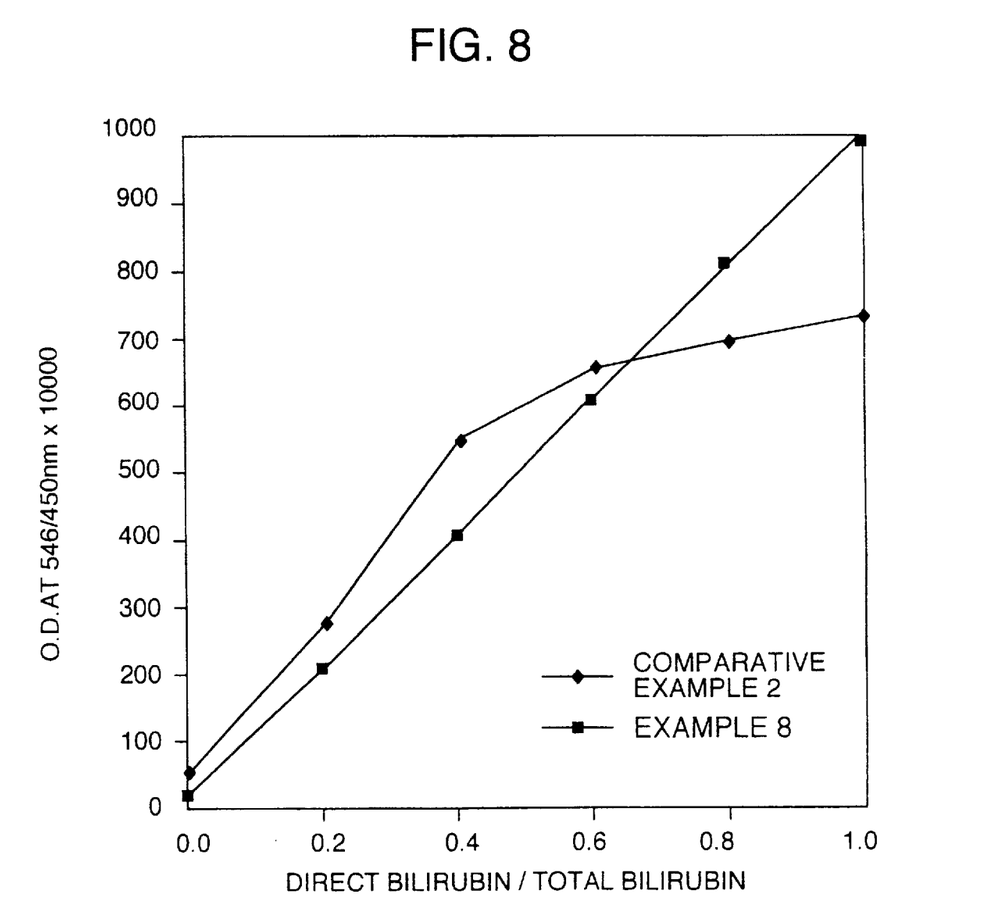
FIG. 8 shows results obtained in Example 8 and Comparative Example 2, wherein a ratio of direct bilirubin to total bilirubin is given on the abscissa and a decrease in the absorbance is given on the ordinate.
Figure 9:
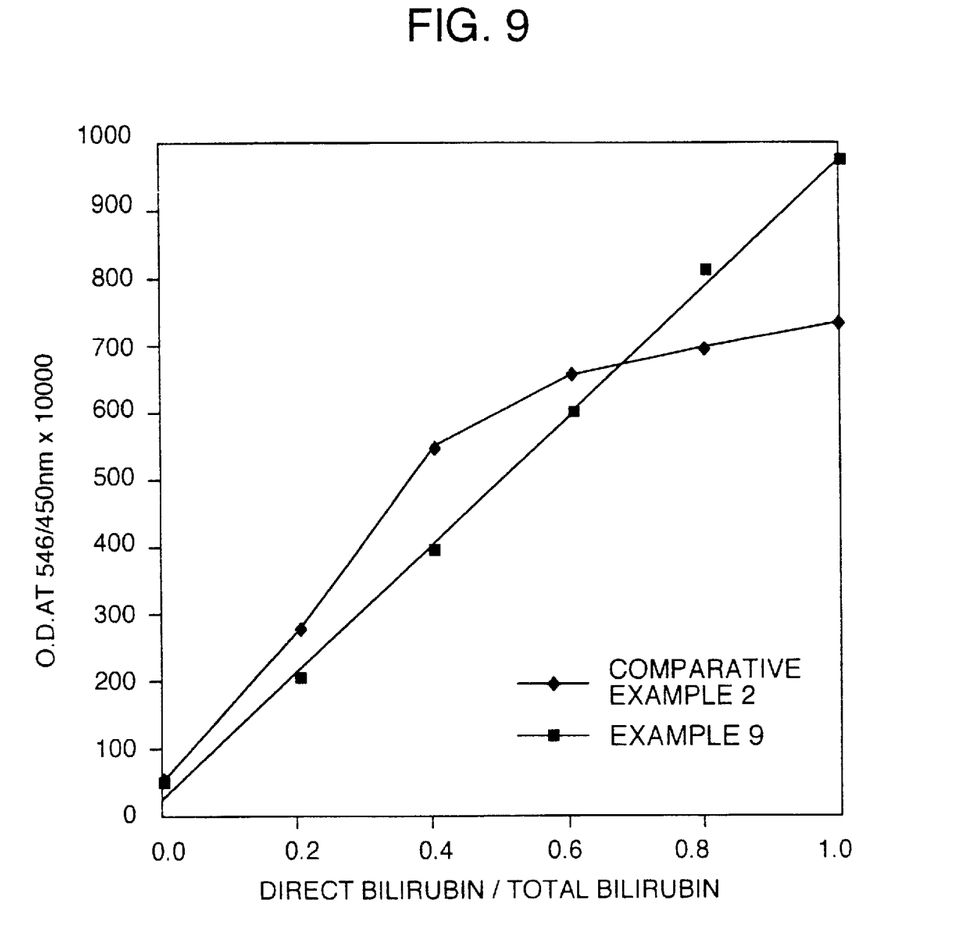
FIG. 9 shows results obtained in Example 9 and Comparative Example 2, wherein a ratio of direct bilirubin to total bilirubin is given on the abscissa and a decrease in the absorbance is given on the ordinate.
Figure 10:
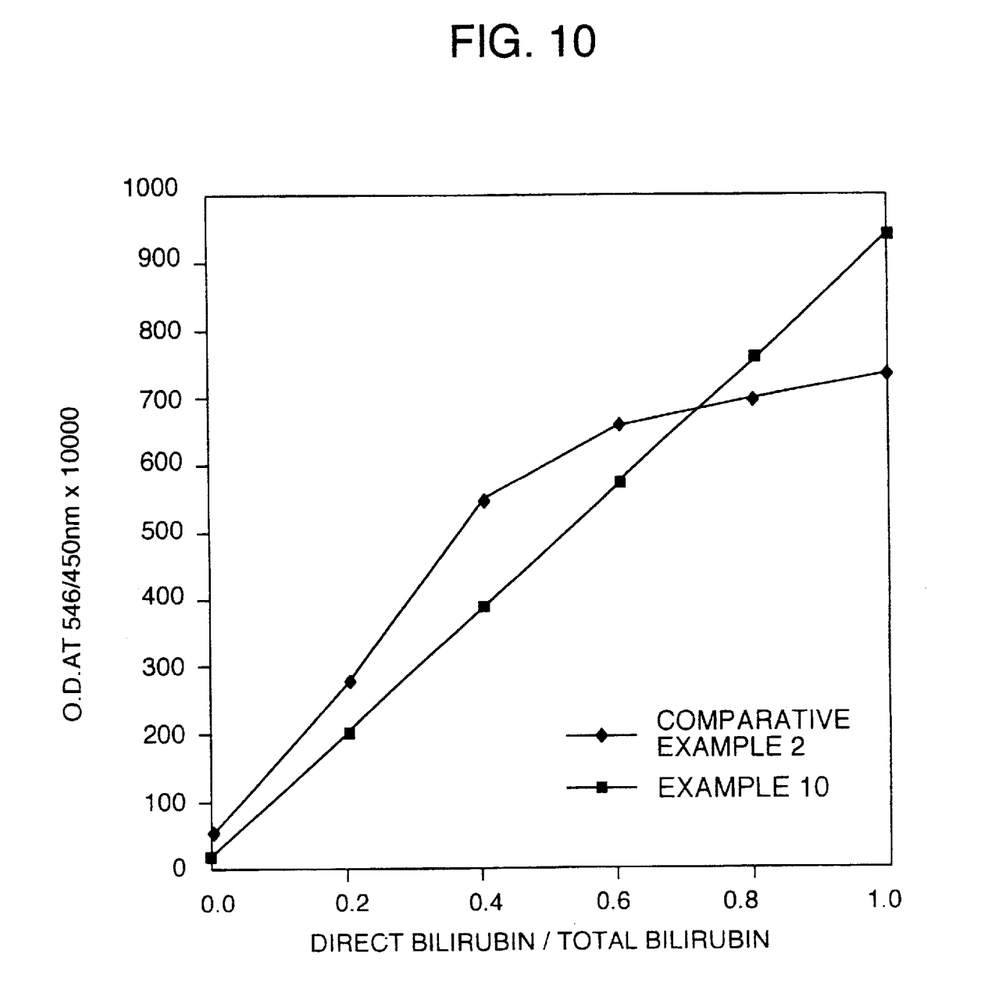
FIG. 10 shows results obtained in Example 10 and Comparative Example 2, wherein a ratio of direct bilirubin to total bilirubin is given on the abscissa and a decrease in the absorbance is given on the ordinate.
Figure 11:
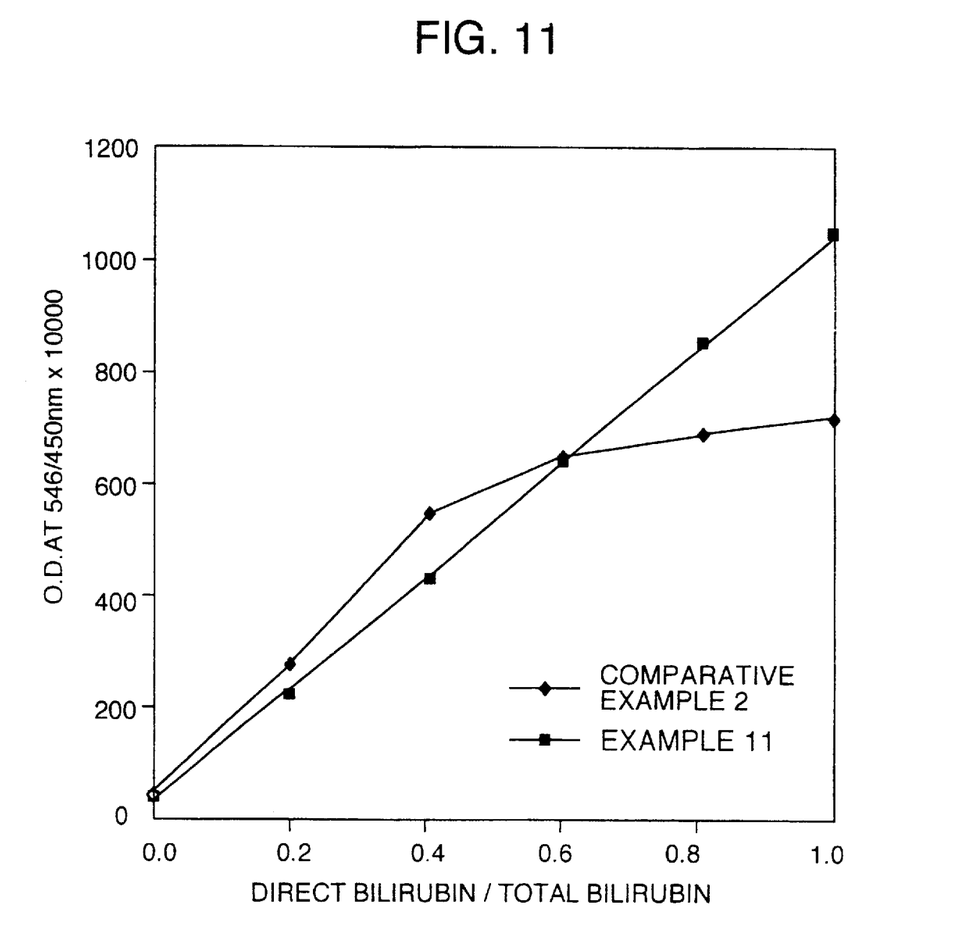
FIG. 11 shows results obtained in Example 11 and Comparative Example 2, wherein a ratio of direct bilirubin to total bilirubin is given on the abscissa and a decrease in the absorbance is given on the ordinate.
Figure 12:
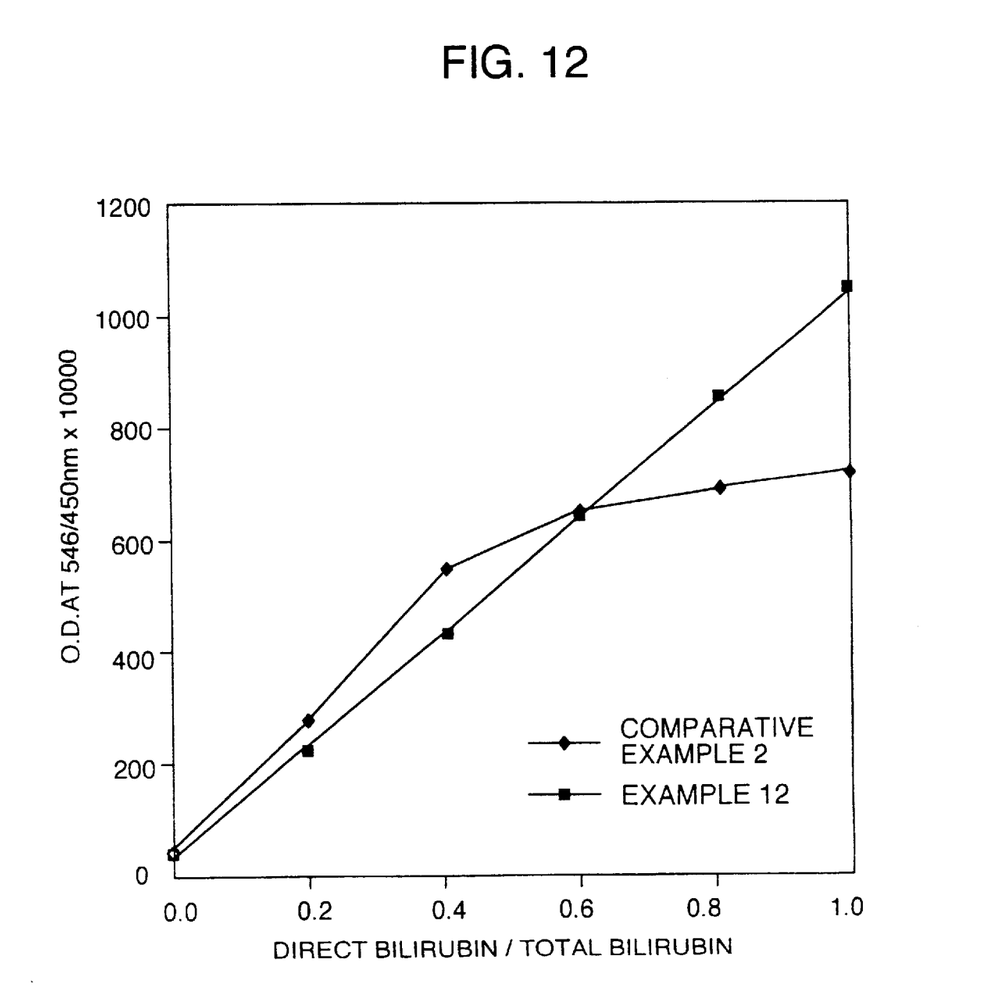
FIG. 12 shows results obtained in Example 12 and Comparative Example 2, wherein a ratio of direct bilirubin to total bilirubin is given on the abscissa and a decrease in the absorbance is given on the ordinate.

The results are shown in FIGS. 7 through 12. In the figures, a ratio of direct bilirubin to total bilirubin is given on the axis of abscissa and a decrease in the absorbance is given on the axis of ordinate. In Examples 7 to 12, which embody the method of the present invention, the absorbance increases in proportion to the amount of direct bilirubin and the working curves show a good linearity of the dilution passing through the origin, indicating that in Examples 7 through 12, direct bilirubin is selectively measured without any interference of indirect bilirubin.

COMPARATIVE EXAMPLE 2

Determination of direct bilirubin in a sample containing direct bilirubin and indirect bilirubin by a conventional method For the purpose of comparison, direct bilirubin in the sample used in Examples 7 to 12 is determined by a conventional method. A method for bilirubin measurement using a bilirubin oxidase under the pH condition of 3.5 to 4.5 is used as the conventional method (Japanese Patent KOKAI (Laid-Open) No. 59-125891, Shogo Otsuji, Clin. Biochem., 21, 33–38 (1988)). That is, the reagents used have the following compositions.

(1) First and second reagent solutions

| First reagent solution by the conventional method | |
| --- | --- |
| Trisodium citrate trihydrate | 17.65 g/l |
| Lactic acid | 30.0 g/l |
| Triton X-100 | 1.0 g/l |
| EDTA.2Na.2H$_2$O | 18.6 mg/l |
| pH 3.70 | |
| Second reagent solution by the conventional method | |
| Trisodium citrate trihydrate | 3.0 g/l |
| Lactic acid | 160 mg/l |
| Triton X-100 | 1.0 g/l |
| CuSO$_4$.5H$_2$O | 1.25 g/l |
| Bilirubin oxidase | 0.2 U/ml |
| pH 6.50 | |

(2) Method

The same conditions as those for measurement described in Example 1 are used, except for using the above reagent solutions.

(3) Results

The results are shown in FIGS. 7 through 12. The results of the conventional method (Comparative Example 2) reveal that no linearity is obtained between the concentration of direct bilirubin in the sample and the absorbance measured, indicating that in the conventional method, direct bilirubin in the sample is not precisely measured due to serious interference of indirect bilirubin in the sample.

EXAMPLES 13 THROUGH 18

Confirmation by HPLC that indirect bilirubin in a sample suspected of containing a high level of bilirubin did not cause any appreciable interference under the conditions for the measurement method of the invention (1) Sample A pool of sera collected from the patients with a high level of bilirubin is used as a sample. The sample is provided for analysis in its intact form, without salting out with sodium sulfate. The intact sample would result in adsorption of globulins in the sample onto a column thereby to promote deterioration of the column but for the purpose of preventing denaturation of bilirubin fractions, the sample is not subjected to any salting-out treatment.

(2) Reagents

The same reagents as used in Examples 1 through 6 are used, respectively, in Example 13 (potassium ions are used as the inhibitor), Example 14 (thiocyanate ions), Example 15 (hydrazide), Example 16 (hydrazide), Example 17 (NADH) and Example 18 (NADPH). In Comparative Example 3, the same reagent as used in Comparative Example 2 is employed.

(3) Oxidation of bilirubin in sample with bilirubin oxidase

To 16 μl of the sample is added 480 μl of the first reagent solution. The mixture is heated at 37° C. for 5 minutes. Then 120 μl of the second reagent solution is added to the mixture. After heating at 37° C. for 5 minutes, 120 μl of 2% ascorbic acid aqueous solution is added to terminate the reaction of bilirubin oxidase.

(4) Analysis by HPLC

The analysis by HPLC is carried out in accordance with the method described in John J. Lauff, Clin. Chem., 28 (4), 629–637 (1982) and changes in the peak area due to indirect bilirubin are examined before and after the reaction. For data before the reaction, the same procedures as in the oxidation described above are performed except that physiological saline is used in place of the second reagent solution. Thus, the peak area based on indirect bilirubin is determined.

Hitachi HPLC System (Column Oven L-7300, UV Detector L-7400, Pump L-7100, Integrator D-7500) equipped with a reversed phase column Lichrspher 100 RP-18 (10 μm, made by Kanto Kagaku K.K.) is used for HPLC.

That is, the solution obtained by the oxidation described above is filtered through a membrane filter of 0.45 μm and 150 μl of the filtrate is flown through the HPLC column, whereby the peak area based on indirect bilirubin after the reaction is measured. Elution is effected by the linear gradient of isopropanol between two solutions, Solution A (950 volume of purified water/50 volume of 2-methoxyethanol, pH 2.1 adjusted with phosphoric acid) and Solution B (950 volume of isopropanol/50 volume of 2-methoxyethanol/2.5 volume of phosphoric acid). The bilirubin fractions are detected at a wavelength of 450 nm.

(5) Results

When the data on the peak area before the reaction is made 100, this data is compared to the data on the peak area based on indirect bilirubin after the reaction to obtain the residual ratio of indirect bilirubin. The results are shown in Table 2. In the present invention, no significant change is observed before and after the reaction in the peak area based on indirect bilirubin. It is thus confirmed that indirect bilirubin is not reacted under the measurement conditions of the present invention. Turning to Comparative Example 3 (conventional method), 16.5% decrease is noted with indirect bilirubin, indicating that a part of indirect bilirubin is reacted under the conditions in the conventional method.

TABLE 2

Residual ratio of indirect bilirubin

| Examples | Peak area based on indirect bilirubin | Residual ratio of indirect bilirubin |
| --- | --- | --- |
| Before reaction | 994970 | 100% |
| Comparative Example 3 | 830862 | 83.5% |
| Before reaction | 875290 | 100% |
| Example 13 | 904927 | 103.4% |
| Example 14 | 895731 | 102.3% |
| Example 15 | 896423 | 102.4% |
| Example 16 | 922454 | 105.4% |
| Example 17 | 882217 | 100.8% |
| Example 18 | 936440 | 98.3% |

According to the present invention, direct bilirubin in a sample can be selectively determined without any interference of indirect bilirubin. Therefore, the present invention makes contribution to the field of clinical tests.

What is claimed is:

1. A method for determination of direct bilirubin which comprises the steps of:

contacting a bilirubin oxidase with a sample suspected of containing bilirubin; and, measuring direct bilirubin in the sample by optical changes of the sample, said bilirubin oxidase being acted in the presence of at least one reaction inhibitor for indirect bilirubin selected from a thiocyanate ion, a hydrazide, reduced nicotinamide adenine dinucleotide, reduced nicotinamide adenine dinucleotide phosphate and a potassium ion of 100 mM to 800 mM.

2. The method for determination of direct bilirubin according to claim 1, wherein a pH value is in a range of 5.0 to 6.0 at the step of contacting a bilirubin oxidase with the sample.

3. A reagent for measurement of direct bilirubin comprising as essential ingredients:

i) a bilirubin oxidase; and, ii) at least one reaction inhibitor for indirect bilirubin selected from a thiocyanate ion, a hydrazide, NADH, NADPH and a potassium ion of 100 mM to 800 mM.

* * * * *